United States Patent [19]

Becker et al.

[11] Patent Number: 4,780,129
[45] Date of Patent: Oct. 25, 1988

[54] CYCLOXEXENONE DERIVATIVES, THEIR MANUFACTURE AND THEIR USE FOR CONTROLLING UNDESIRABLE PLANT GROWTH

[75] Inventors: Rainer Becker, Bad Duerkheim; Dieter Jahn, Edingen-Neckarhausen; Ulrich Schirmer, Heidelberg; Michael Keil, Freinsheim; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 14,146

[22] Filed: Feb. 13, 1987

Related U.S. Application Data

[63] Continuation of Ser. No. 794,454, Nov. 4, 1985, abandoned.

[30] Foreign Application Priority Data

Nov. 6, 1984 [DE] Fed. Rep. of Germany ....... 3440410

[51] Int. Cl.$^4$ ............ A01N 33/24; A01N 31/04; C07C 121/46; C07C 121/48
[52] U.S. Cl. .......................... 71/121; 71/97; 71/105; 71/106; 71/113; 558/430; 558/431; 558/432; 558/434; 560/125; 560/126; 562/507; 562/508; 564/256; 568/367
[58] Field of Search ........... 558/430, 431, 432, 433, 558/434; 71/105, 97, 121; 560/125; 562/507; 564/256; 568/367

[56] References Cited

U.S. PATENT DOCUMENTS

| | | | |
|---|---|---|---|
| 3,950,420 | 4/1976 | Sawaki et al. | 71/105 X |
| 4,440,566 | 4/1984 | Luo | 560/125 X |
| 4,515,729 | 5/1985 | Iwataki et al. | 71/105 X |
| 4,517,013 | 5/1985 | Becker et al. | 71/105 X |
| 4,568,383 | 2/1986 | Jahn et al. | 560/125 X |
| 4,584,013 | 4/1986 | Brunner | 562/507 X |
| 4,617,050 | 10/1986 | Jahn et al. | 71/98 |
| 4,618,360 | 10/1986 | Brunner | 562/507 X |

FOREIGN PATENT DOCUMENTS

| | | | |
|---|---|---|---|
| 0070495 | 1/1983 | European Pat. Off. | 71/105 |
| 19945 | 2/1979 | Japan . | |
| 63052 | 5/1979 | Japan . | |
| 57-045143 | 3/1982 | Japan | 71/105 |
| 1461170 | 1/1977 | United Kingdom . | |

OTHER PUBLICATIONS

Buyck, et al.; Tetrahedron Letters, 29, pp. 2491-2492 (1975).
Org. Synth.; Coll. Vol. II, pp. 200-203, (date unknown).
Krapcho; Synthesis, (1982), pp. 805 to 822.
Sawaki, et al., C. A., 86 (1977), 86:1893182.

Primary Examiner—Joseph Paul Brust
Attorney, Agent, or Firm—Keil & Weinkauf

[57] ABSTRACT

Cyclohexenone derivatves of the formula

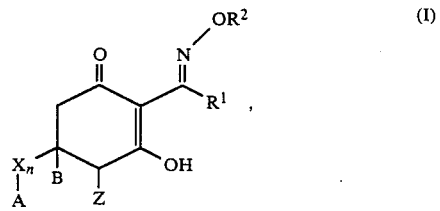

where $R^1$ is alkyl, $R^2$ is alkyl, unsubstituted or substituted alkenyl or alkynyl, A is alkoxycarbonyl, carboxyl, cyano or trifluoromethyl, B is hydrogen or methyl, X is straight-chain, branched or cyclic alkylene, Z is hydrogen or alkoxycarbonyl and n is 0 or 1, and salts thereof, and their use for combatting unwanted plant growth.

11 Claims, No Drawings

CYCLOXEXENONE DERIVATIVES, THEIR MANUFACTURE AND THEIR USE FOR CONTROLLING UNDESIRABLE PLANT GROWTH

This application is a continuation of application Ser. No. 794,454, filed on Nov. 4, 1985, now abandoned.

The present invention relates to cyclohexenone derivatives, herbicides which contain these compounds as active ingredients, and a method of controlling undesirable plant growth.

It is known that cyclohexenone derivatives possess herbicidal activity (DE-A-2 439 104 and JP-A-19 945/1979).

We have found that cyclohexenone derivatives of the formula I

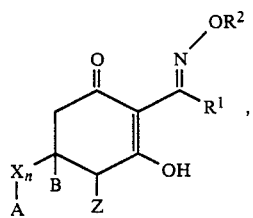

where $R^1$ is $C_1$–$C_4$-alkyl, $R^2$ is $C_1$–$C_4$-alkyl, unsubstituted or halogen-substituted $C_3$–$C_5$-alkenyl or $C_3$–$C_5$-alkenyl, A is $C_2$–$C_5$-alkoxycarbonyl, carboxyl, cyano or trifluoromethyl, B is hydrogen or methyl, X is straight-chain, branched or cyclic alkylene of not more than 7 carbon atoms, Z is hydrogen or $C_2$–$C_5$-alkoxycarbonyl and n is 0 or 1, with the proviso that n is not 0 when A is alkoxycarbonyl or cyano, and salts of these compounds have a good herbicidal action preferentially against species from the family consisting of the grasses (Gramineae). They are tolerated by, and therefore selective in, broad-leaved crops and monocotyledon plants not belonging to the Gramineae, and are selective in gramineous crops, such as wheat and rice, and at the same time have a herbicidal action against undesirable grasses.

The cyclohexenone derivatives of the formula I can occur in tautomeric forms, all of which are embraced by the claim:

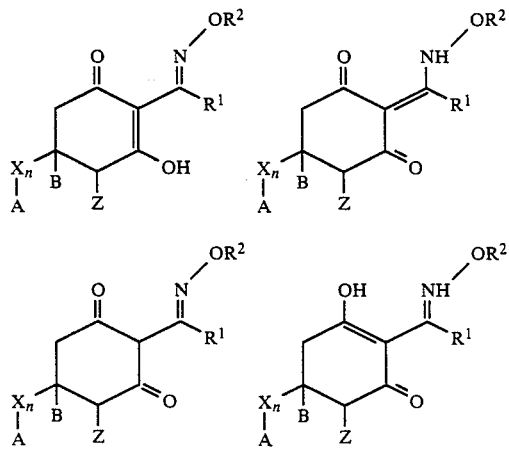

In formula I, $R^1$ is straight-chain or branched $C_1$–$C_4$-alkyl, preferably $C_2$- or $C_3$-alkyl, eg. methyl, ethyl, n-propyl, sec.-butyl. or n-butyl, $R^2$ is straight-chain or branched $C_1$–$C_4$-alkyl, $C_3$–$C_5$-alkenyl which may be substituted by halogen, in particular chlorine, or $C_3$–$C_5$-alkynyl, eg. methyl, ethyl, n-propyl, n-butyl, allyl, propargyl, 2-chloroallyl or 3-chloroallyl (cis or trans), A is $C_2$–$C_5$-alkoxycarbonyl, eg. methoxycarbonyl or ethoxycarbonyl, or is carboxyl, cyano or trifluoromethyl, B is hydrogen or methyl, preferably the former, X is straight-chain or branched alkylene of not more than 7 carbon atoms or cyclic alkylene of 3 to 7 carbon atoms, eg. methylene, ethylene, trimethylene, tetramethylene, methylmethylene, methylethylene, 2,5-dimethylpentamethylene, 1,4-cyclohexylene, 1,3-cyclohexylene, 1,2-cyclohexylene or 1,2-cyclopropylene, and, finally, Z is hydrogen or $C_2$–$C_5$-alkoxycarbonyl, eg. methoxycarbonyl or ethoxycarbonyl, preferably methoxycarbonyl and particularly preferably hydrogen.

Suitable salts of the compounds of the formula I are those which can be used in agriculture, for example the alkali metal salts, in particular the potassium or sodium salts, alkaline earth metal salts, in particular calcium, magnesium or barium salts, manganese salts, copper salts, zinc salts and iron salts, as well as ammonium, sulfonium and phosphonium salts.

The novel cyclohexenone derivatives of the formula I are obtained by reacting a carbonyl compound of the formula II

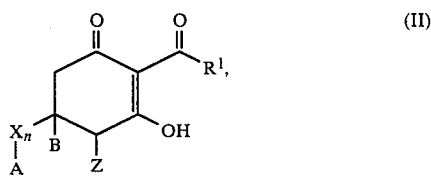

where $R^1$, A, B, Z, X and n have the above meanings, with a hydroxylamine derivative of the formula $R^2ONH_3Y$ where $R^2$ has the above meanings and Y is an anion, eg. chloride, bromide or sulfate. The carbonyl compounds of the formula II are likewise novel.

The reaction is advantageously carried out in the heterogeneous phase in an inert diluent at from 0° to about 80° C. or from 0° C. to the boiling point of the reaction mixture in presence of a base. Examples of suitable bases are carbonates, bicarbonates, acetates, alcoholates, hydroxides and oxides of alkali metals and alkaline earth metals, in particular of sodium, potassium, magnesium and calcium. It is also possible to use an organic base, such as pyridine or a tertiary amine.

The reaction takes place readily at a pH of from 2 to 9, preferably from 4 to 6, in particular from 4.5 to 5.5, the pH advantageously being established by adding an acetate, for example an alkali metal acetate, in particular sodium acetate or potassium acetate, or a mixture of the two salts. The alkali metal acetate is added in an amount of, for example, from 0.5 to 2 moles per mole of the ammonium compound of the formula $R^2ONH_3Y$.

Examples of suitable solvents are dimethylsulfoxide, alcohols, such as methanol, ethanol or isopropanol, benzene, hydrocarbons and chlorohydrocarbons, such as chloroform, dichloroethane, hexane or cyclohexane, esters, such as ethyl acetate, and cyclic ethers, such as dioxane and tetrahydrofuran.

The reaction is complete after a few hours, and the product can then be isolated by evaporating down the reaction mixture, adding water and extracting the mixture with a non-polar solvent, such as methylene chloride, and distilling off the solvent under reduced pressure.

The compounds of the formula I may furthermore be obtained by reacting a carbonyl compound of the formula II with a hydroxylamine of the formula $R^2ONH_2$, where $R^2$ has the above meanings, in an inert diluent at from 0° C. to the boiling point of the reaction mixture, advantageously at about 15°–70° C. The hydroxylamine can, if required, also be used in the form of an aqueous solution.

Examples of suitable solvents for this reaction are alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

Finally, the carbonyl compound of the formula II may also be reacted with an unsubstituted hydroxylammonium salt of the formula $HONH_3Y$, where Y is an anion (eg. chloride, bromide or sulfate), in the presence of a solvent and of a base, the reaction conditions being similar to those for the abovementioned reaction with the ammonium compound of the formula $R^2ONH_3Y$. The oxime thus obtained is then converted to the desired compound of the formula I using an alkylating agent of the formula $R^2Y'$, where $R^2$ has the above meanings and $Y'$ is a leaving group (eg. chlorine, bromine, iodine or $R^2OSO_3$), at from 0° to 100° C. in an inert solvent, such as dioxane, tetrahydrofuran or N,N-dimethylformamide, in the presence of absence of a base (cf. the bases stated above).

The alkali metal salts of the cyclohexenone derivatives of the formula I can be obtained by treating these compounds with sodium hydroxide or potassium hydroxide in aqueous solution or in an organic solvent, such as methanol, ethanol or acetone. Sodium alcoholates and potassium alcoholates may also be used for forming salts.

The other metal salts, eg. the manganese, copper, zinc, iron, calcium, magnesium and barium salts, can be prepared from the sodium salts by reaction with the corresponding metal chlorides in aqueous solution. Ammonium, sulfonium and phosphonium salts can be obtained by reacting a compound of the formula I with an ammonium, sulfonium or phosphonium hydroxide, if necessary in aqueous solution.

The novel carbonyl compounds of the formula II can be prepared from cyclohexanediones of the formula III, which can also occur in the tautomeric form IIIa

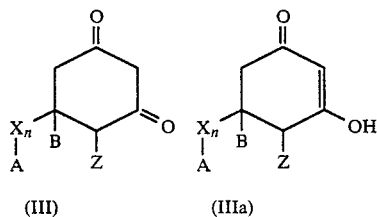

the preparation being carried out using a method known from the literature (Tetrahedron Lett. 29 (1975), 2491).

It is also possible to prepare the carbonyl compounds of the formula II via the enol-ester intermediates IV, which are obtained in the reaction of a derivative III with an acyl chloride and undergo a rearrangement reaction in the presence of an imidazole or pyridine derivative (JP-A-63 052/1979).

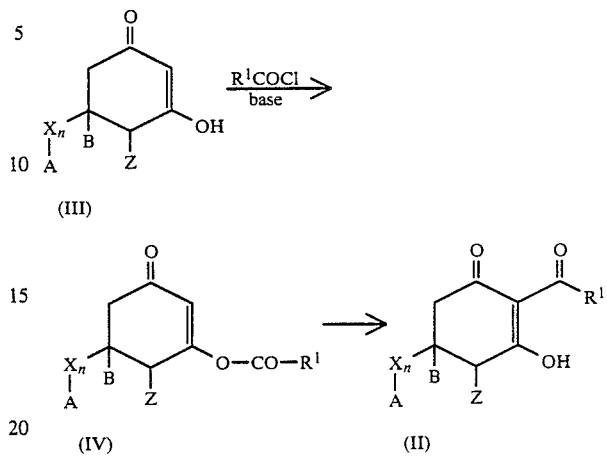

The compounds of the formula III are obtained by a conventional method (Org. Synth. Coll. II, page 200). In addition to alkaline hydrolysis followed by decarboxylation under acidic conditions, which is the method described there, the activated ester group can also be eliminated in a neutral medium using dimethyl sulfoxide/water/sodium chloride (Synthesis 1982, 805), which is particularly advantageous where other labile groups are present in the molecule.

As can be seen from the above statements, the novel carbonyl compounds of the formula II are useful intermediates for the synthesis of herbicidal cyclohexeone derivatives of the formula I.

The Examples which follow illustrate the preparation of the novel cyclohexenone derivatives of the formula I.

EXAMPLE 1

9.21 g of 2-butyryl-5-(4-trifluoromethylcyclohexyl)-cyclohexane-1,3-dione were taken up in 100 ml of methanol, 2.94 g of ethoxyammonium chloride and 2.52 g of sodium bicarbonate were added and the mixture was stirred at room temperature for 20 hours, after which it was poured into water and extracted with methylene chloride, and the extract was evaporated down. 7.9 g of 2-(1-ethoxyaminobutylidene)-5-(4-trifluoromethylcyclohexyl)-cyclohexane-1,3-dione (compound No. 1) were obtained.

| $_1$HNMR (in $CDCl_3$/TMS) = | 4.08 (q) [2 protons] |
|---|---|
| | 1.90 (m) [cyclohexyl protons] |
| | 0.92 (t) [3 protons] |

The cyclohexenone derivatives below, of the formula I

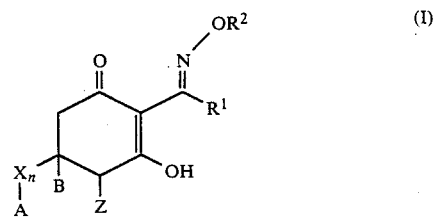

can be prepared by a similar method.

In the substituents X listed in Table I below, the left-hand bond is to be linked to the cyclohexane ring in each case.

TABLE 1

| Compound no. | A | X | n | B | Z | $R^1$ | $R^2$ | Physical data |
|---|---|---|---|---|---|---|---|---|
| 2 | $CF_3$ | 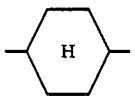 | 1 | H | H | n-$C_3H_7$ | $CH_2CH=CH_2$ | $n_D^{22}$ 1.4941 |
| 3 | $COOCH_3$ | —$(CH_2)_4$— | 1 | H | $COOCH_3$ | n-$C_3H_7$ | $C_2H_5$ | $n_D^{25}$ 1.5067 |
| 4 | $COOCH_3$ | —$(CH_2)_4$— | 1 | H | $COOCH_3$ | n-$C_3H_7$ | $CH_2CH=CH_2$ | $n_D^{25}$ 1.5108 |
| 5 | $COOCH_3$ | —$(CH_2)_4$— | 1 | H | $COOCH_3$ | $C_2H_5$ | $C_2H_5$ | $n_D^{25}$ 1.5062 |
| 6 | $COOCH_3$ | —$(CH_2)_4$— | 1 | H | $COOCH_3$ | $C_2H_5$ | $CH_2CH=CH_2$ | $n_D^{24}$ 1.5124 |
| 7 | $COOCH_3$ | —$CH_2CH(CH_3)$— | 1 | H | $COOCH_3$ | $C_2H_5$ | $C_2H_5$ | $n_D^{23}$ 1.5030 |
| 8 | $COOCH_3$ | —$CH_2CH(CH_3)$— | 1 | H | $COOCH_3$ | $C_2H_5$ | $CH_2CH=CH_2$ | $n_D^{23}$ 1.5074 |
| 9 | $COOCH_3$ | —$CH_2CH(CH_3)$— | 1 | H | $COOCH_3$ | n-$C_3H_7$ | $C_2H_5$ | $n_D^{22}$ 1.5025 |
| 10 | $COOCH_3$ | —$CH_2CH(CH_3)$— | 1 | H | $COOCH_3$ | n-$C_3H_7$ | $CH_2CH=CH_2$ | $n_D^{22}$ 1.5070 |
| 11 | $COOCH_3$ | —$CH_2CH(CH_3)$— | 1 | H | H | n-$C_3H_7$ | $C_2H_5$ | NMR see below |
| 12 | CN | —$CH(CH_3)CH_2$— | 1 | H | H | n-$C_3H_7$ | $CH_2CH=CHCl$ | $n_D^{23}$ 1.5398 |
| 13 | CN | —$CH(CH_3)CH_2$— | 1 | H | H | n-$C_3H_7$ | $C_2H_5$ | $n_D^{23}$ 1.5213 |
| 14 | CN | —$CH(CH_3)CH_2$— | 1 | H | H | n-$C_3H_7$ | $CH_2CH=CH_2$ | $n_D^{23}$ 1.5271 |
| 15 | $COOC_2H_5$ |  | 1 | H | $COOCH_3$ | n-$C_3H_7$ | $C_2H_5$ | $n_D^{24}$ 1.5103 |
| 16 | $COOC_2H_5$ |  | 1 | H | $COOCH_3$ | n-$C_3H_7$ | $CH_2CH=CH_2$ | $n_D^{24}$ 1.5144 |
| 17 | $CF_3$ | | 0 | $CH_3$ | H | n-$C_3H_7$ | $CH_2CH=CH_2$ | $n_D^{21.5}$ 1.4829 |
| 18 | $CF_3$ | | 0 | $CH_3$ | H | n-$C_3H_7$ | $C_2H_5$ | $n_D^{21.5}$ 1.4758 |
| 19 | $CF_3$ | | 0 | $CH_3$ | $COOCH_3$ | n-$C_3H_7$ | $CH_2CH=CH_2$ | $n_D^{22}$ 1.4890 |
| 20 | $CF_3$ | | 0 | $CH_3$ | $COOCH_3$ | n-$C_3H_7$ | $C_2H_5$ | |
| 21 | COOH |  | 1 | H | H | n-$C_3H_7$ | $C_2H_5$ | NMR see below |
| 22 | COOH |  | 1 | H | H | n-$C_3H_7$ | $CH_2CH=CH_2$ | NMR see below |
| 23 | $COOCH_3$ | —$CH_2CH(CH_3)(CH_2)_3$— | 1 | H | $COOCH_3$ | n-$C_3H_7$ | $C_2H_5$ | $n_D^{29}$ 1.4930 |
| 24 | $COOCH_3$ | —$CH_2CH(CH_3)(CH_2)_3$— | 1 | H | $COOCH_3$ | n-$C_3H_7$ | $CH_2CH=CH_2$ | $n_D^{29}$ 1.5000 |
| 25 | $COOCH_3$ | —$CH_2CH(CH_3)(CH_2)_3$— | 1 | H | H | n-$C_3H_7$ | $C_2H_5$ | $n_D^{24}$ 1.4972 |
| 26 | $COOCH_3$ | —$CH_2CH(CH_3)(CH_2)_3$— | 1 | H | H | n-$C_3H_7$ | $CH_2CH=CH_2$ | $n_D^{24}$ 1.5031 |
| 27 | $COOCH_3$ | —$CH_2CH(CH_3)(CH_2)_3$— | 1 | H | H | n-$C_3H_7$ | $CH_2C≡CH$ | $n_D^{22}$ 1.5090 |
| 28 | $COOC(CH_3)_3$ | —$CH(CH_3)$— | 1 | H | H | n-$C_3H_7$ | $C_2H_5$ | $n_D^{23}$ 1.4978 |
| 29 | $COOCH_3$ | —$CH_2CH(CH_3)(CH_2)_2CH(CH_3)$— | 1 | H | H | n-$C_3H_7$ | $C_2H_5$ | NMR see below |
| 30 | $COOCH_3$ | —$CH_2CH(CH_3)(CH_2)_2CH(CH_3)$— | 1 | H | H | n-$C_3H_7$ | $CH_2CH=CH_2$ | NMR see below |
| 31 | $CF_3$ | 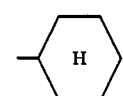 | 1 | H | H | n-$C_3H_7$ | $C_2H_5$ | NMR see below |
| 32 | $CF_3$ | 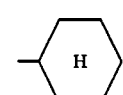 | 1 | H | H | n-$C_3H_7$ | $CH_2CH=CH_2$ | NMR see below |
| 33 | $CF_3$ | 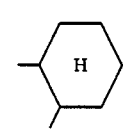 | 1 | H | H | n-$C_3H_7$ | n-$C_3H_7$ | NMR see below |

TABLE 1-continued

| Compound no. | A | X | n | B | Z | R¹ | R² | Physical data |
|---|---|---|---|---|---|---|---|---|
| 34 | $CF_3$ | 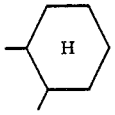 | 1 | H | H | $n\text{-}C_3H_7$ | $n\text{-}C_4H_9$ | |
| 35 | $CF_3$ | 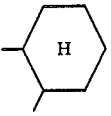 | 1 | H | H | $n\text{-}C_3H_7$ | $CH_2CH{=}CHCl$ (trans) | |
| 36 | $CF_3$ | 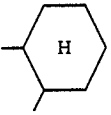 | 1 | H | H | $C_2H_5$ | $C_2H_5$ | |
| 37 | $COOCH_3$ | $-(CH_2)_4-$ | 1 | H | H | $n\text{-}C_3H_7$ | $C_2H_5$ | NMR see below |
| 38 | $COOCH_3$ | $-(CH_2)_4-$ | 1 | H | H | $n\text{-}C_3H_7$ | $CH_2CH{=}CH_2$ | |
| 39 | $COOCH_3$ | $-CH_2CH(CH_3)-$ | 1 | H | H | $n\text{-}C_3H_7$ | $CH_2CH{=}CHCH_3$ (trans) | |
| 40 | $COOCH_3$ | $-CH_2CH(CH_3)-$ | 1 | H | H | $n\text{-}C_3H_7$ | $CH_2CH{=}CH_2$ | |
| 41 | $COOCH_3$ | $-CH_2CH(CH_3)-$ | 1 | H | H | $n\text{-}C_3H_7$ | $CH_2CH{=}CHCl$ | |
| 42 | $COOCH_3$ | $-CH_2CH(CH_3)-$ | 1 | H | H | $C_2H_5$ | $C_2H_5$ | |
| 43 | $CF_3$ | 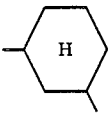 | 1 | H | H | $n\text{-}C_3H_7$ | $CH_2CH{=}CH_2$ | |
| 44 | $CF_3$ | 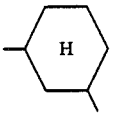 | 1 | H | H | $n\text{-}C_3H_7$ | $C_2H_5$ | |
| 45 | $COOCH_3$ | 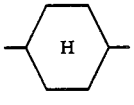 | 1 | H | H | $n\text{-}C_3H_7$ | $C_2H_5$ | |
| 46 | $COOCH_3$ | 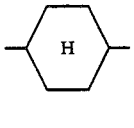 | 1 | H | H | $n\text{-}C_3H_7$ | $CH_2CH{=}CH_2$ | |
| 47 | $COOCH_3$ | 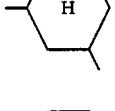 | 1 | H | H | $n\text{-}C_3H_7$ | $C_2H_5$ | |
| 48 | $COOCH_3$ | 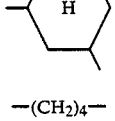 | 1 | H | H | $n\text{-}C_3H_7$ | $CH_2CH{=}CH_2$ | |
| 49 | COOH | $-(CH_2)_4-$ | 1 | H | H | $C_2H_5$ | $CH_2CH{=}CHCl$ | NMR see below |
| 50 | COOH | $-(CH_2)_4-$ | 1 | H | H | $C_2H_5$ | $CH_2CH{=}CHCl$ | NMR see below |
| 51 | COOH | $-(CH_2)_4-$ | 1 | H | H | $n\text{-}C_3H_7$ | $C_2H_5$ | NMR see below |
| 52 | COOH | $-(CH_2)_4-$ | 1 | H | H | $n\text{-}C_3H_7$ | $CH_2CH{=}CH_2$ | NMR see below |
| 53 | COOH | $-(CH_2)_4-$ | 1 | H | H | $C_2H_5$ | $CH_2CH{=}CH_2$ | NMR see below |
| 54 | $COOCH_3$ | $-(CH_2)_4-$ | 1 | H | H | $C_2H_5$ | $CH_2CH{=}CHCl$ | NMR see below |
| 55 | $COOCH_3$ | $-(CH_2)_4-$ | 1 | H | H | $C_2H_5$ | $C_2H_5$ | NMR see below |
| 56 | $COOCH_3$ | $-(CH_2)_4-$ | 1 | H | H | $n\text{-}C_3H_7$ | $CH_2CH{=}CHCl$ (trans) | NMR see below |
| 57 | $COO\text{-}n\text{-}C_4H_9$ | $-(CH_2)_4-$ | 1 | H | H | $n\text{-}C_3H_7$ | $C_2H_5$ | NMR see below |

TABLE 1-continued

| Compound no. | A | X | n | B | Z | $R^1$ | $R^2$ | Physical data |
|---|---|---|---|---|---|---|---|---|
| 58 | COO—n-$C_4H_9$ | —$(CH_2)_4$— | 1 | H | H | $C_2H_5$ | $C_2H_5$ | NMR see below |
| 59 | COO—n-$C_4H_9$ | —$(CH_2)_4$— | 1 | H | H | n-$C_3H_7$ | $CH_2CH=CHCl$ | NMR see below |
| 60 | COO—n-$C_4H_9$ | —$(CH_2)_4$— | 1 | H | H | $C_2H_5$ | $CH_2CH=CHCl$ (trans) | NMR see below |
| 61 | COOH | —$CH_2CH(CH_3)$— | 1 | H | H | $C_2H_5$ | $C_2H_5$ | NMR see below |
| 62 | COO—n-$C_4H_9$ | —$CH_2CH(CH_3)$— | 1 | H | H | $C_2H_5$ | $C_2H_5$ | NMR see below |
| 63 | COOH | —$CH_2CH(CH_3)$— | 1 | H | H | n-$C_3H_7$ | $C_2H_5$ | NMR see below |
| 64 | COOH | —$CH_2(C_2H_5)(CH_2)_2$— | 1 | H | H | $C_2H_5$ | $C_2H_5$ | NMR see below |
| 65 | $COOCH_3$ | —$(CH_2)_2CH(C_2H_5)$— | 1 | H | H | $C_2H_5$ | $C_2H_5$ | |
| 66 | $COOCH_3$ | —$(CH_2)_2CH(C_2H_5)$— | 1 | H | H | $C_2H_5$ | $CH_2CH=CHCl$ (trans) | |
| 67 | $COOCH_3$ | —$(CH_2)_2$— | 1 | H | H | $CH_3$ | $C_2H_5$ | |
| 68 | $COOCH_3$ | —$(CH_2)_2$— | 1 | H | H | $C_2H_5$ | $C_2H_5$ | |
| 69 | $COOCH_3$ | —$(CH_2)_2$— | 1 | H | H | n-$C_3H_7$ | $C_2H_5$ | |
| 70 | COOH | —$(CH_2)_2$— | 1 | H | H | n-$C_3H_7$ | $C_2H_5$ | |
| 71 | COOH | —$(CH_2)_2$— | 1 | H | H | $C_2H_5$ | $C_2H_5$ | |
| 72 | COOH | —$CH_2$— | 1 | H | H | $C_2H_5$ | $C_2H_5$ | |
| 73 | COOH | —$CH_2$— | 1 | H | H | $C_2H_5$ | $CH_2-CH=CH_2$ | |
| 74 | COOH | —$CH_2$— | 1 | H | H | n-$C_3H_7$ | $C_2H_5$ | |
| 75 | COOH | —$CH(CH_3)CH_2$— | 1 | H | H | $C_2H_5$ | $C_2H_5$ | |
| 76 | COOH | —$CH(CH_3)CH_2$— | 1 | H | H | n-$C_3H_7$ | $C_2H_5$ | |
| 77 | $COOCH_3$ | —$CH(CH_3)CH_2$— | 1 | H | H | $C_2H_5$ | $C_2H_5$ | |
| 78 | COO—n-$C_3H_7$ | —$CH(CH_3)CH_2$— | 1 | H | H | $C_2H_5$ | $C_2H_5$ | |

Manufacture of compound no. 102

48.2 g of 2-butyryl-4-methoxycarbonyl-5-(tetramethylenemethoxycarbonyl)cyclohexane-1,3-dione and 305 ml of 10 wt% aqueous potassium hydroxide solution were stirred for 48 hours at room temperature. After extraction with dichloromethane, the aqueous phase was acidified with hydrochloric acid to pH 1. The mixture was then heated to 80° C. and stirred at this temperature for 1 hour. The mixture was allowed to cool, and was then extracted twice with dichloromethane, the organic phase was dried over sodium sulfate, and the solvent was distilled off. 36 g of 2-butyryl-5-(tetramethylenecarboxy)-cyclohexane-1,3-dione were obtained.

The compound may be purified by recrystallization from ligroin (m.p.: 64° C.).

The carbonyl compounds of the formula II

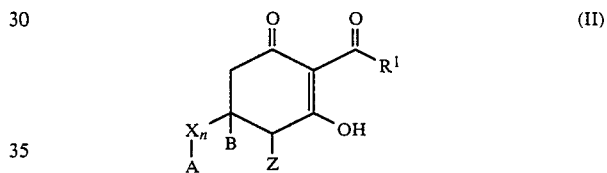

(II)

listed in Table 2 below and which serve as intermediates for the compounds of the formula I may be obtained analogously.

In this table too, the left-hand bond of substituents X is to be linked to the cyclohexane ring.

TABLE 2

| Compound no. | A | X | n | B | Z | $R^1$ | Physical data |
|---|---|---|---|---|---|---|---|
| 79 | $CF_3$ | ⬡H | 1 | H | H | n-$C_3H_7$ | NMR see below |
| 80 | $COOCH_3$ | —$(CH_2)_4$— | 1 | H | $COOCH_3$ | n-$C_3H_7$ | NMR see below |
| 81 | $COOCH_3$ | —$(CH_2)_4$— | 1 | H | $COOCH_3$ | $C_2H_5$ | NMR see below |
| 82 | $COOCH_3$ | —$CH_2CH(CH_3)$— | 1 | H | $COOCH_3$ | $C_2H_5$ | NMR see below |
| 83 | $COOCH_3$ | —$CH_2CH(CH_3)$— | 1 | H | $COOCH_3$ | n-$C_3H_7$ | NMR see below |
| 84 | CN | —$CH(CH_3)CH_2$— | 1 | H | H | n-$C_3H_7$ | NMR see below |
| 85 | $COOC_2H_5$ | △ | 1 | H | $COOCH_3$ | n-$C_3H_7$ | NMR see below |
| 86 | $CF_3$ | | 0 | $CH_3$ | H | n-$C_3H_7$ | NMR see below |
| 87 | $CF_3$ | △ | 0 | $CH_3$ | $COOCH_3$ | n-$C_3H_7$ | NMR see below |
| 88 | COOH | | 1 | H | H | n-$C_3H_7$ | NMR see below |
| 89 | $COOCH_3$ | —$CH_2CH(CH_3)(CH_2)_3$— | 1 | H | $COOCH_3$ | n-$C_3H_7$ | NMR see below |
| 90 | $COOCH_3$ | —$CH_2CH(CH_3)(CH_2)_3$— | 1 | H | H | n-$C_3H_7$ | NMR see below |
| 91 | $COOC(CH_3)_3$ | —$CH_2CH(CH_3)$— | 1 | H | H | n-$C_3H_7$ | NMR see below |
| 92 | $COOCH_3$ | —$CH_2CH(CH_3)(CH_2)_2CH(CH_3)$— | 1 | H | H | n-$C_3H_7$ | NMR see below |

TABLE 2-continued

| Compound no. | A | X | n | B | Z | R[1] | Physical data |
|---|---|---|---|---|---|---|---|
| 93 | CF$_3$ | (cyclohexyl-H) | 1 | H | H | n-C$_3$H$_7$ | |
| 94 | CF$_3$ | (cyclohexyl-H) | 1 | H | H | C$_2$H$_5$ | |
| 95 | COOCH$_3$ | —(CH$_2$)$_4$— | 1 | H | H | n-C$_3$H$_7$ | |
| 96 | COOCH$_3$ | —CH$_2$CH(CH$_3$)— | 1 | H | H | n-C$_3$H$_7$ | |
| 97 | COOCH$_3$ | —CH$_2$CH(CH$_3$)— | 1 | H | H | C$_2$H$_5$ | |
| 98 | CF$_3$ | (cyclohexyl-H) | 1 | H | H | n-C$_3$H$_7$ | |
| 99 | COOCH$_3$ | (cyclohexyl-H) | 1 | H | H | n-C$_3$H$_7$ | |
| 100 | COOCH$_3$ | (cyclohexyl-H) | 1 | H | H | n-C$_3$H$_7$ | |
| 101 | COOH | —(CH$_2$)$_4$— | 1 | H | H | C$_2$H$_5$ | m.p.: 97–98° C. |
| 102 | COOH | —(CH$_2$)$_4$— | 1 | H | H | n-C$_3$H$_7$ | m.p.: 64° C. |
| 103 | COOCH$_3$ | —(CH$_2$)$_4$— | 1 | H | H | C$_2$H$_5$ | |
| 104 | COO—n-C$_4$H$_9$ | —(CH$_2$)$_4$— | 1 | H | H | n-C$_3$H$_7$ | |
| 105 | COO—n-C$_4$H$_9$ | —(CH$_2$)$_4$— | 1 | H | H | C$_2$H$_5$ | |
| 106 | COOH | —CH$_2$CH(CH)$_3$— | 1 | H | H | C$_2$H$_5$ | NMR see below |
| 107 | COO—n-C$_4$H$_9$ | —CH$_2$CH(CH$_3$)— | 1 | H | H | C$_2$H$_5$ | |
| 108 | COOH | —CH$_2$CH(CH$_3$)— | 1 | H | H | n-C$_3$H$_7$ | NMR see below |
| 109 | COOH | —CH(C$_2$H$_5$)(CH$_2$)$_2$— | 1 | H | H | C$_2$H$_5$ | NMR see below |
| 110 | COOCH$_3$ | —(CH$_2$)$_2$CH(C$_2$H$_5$)— | 1 | H | H | C$_2$H$_5$ | |
| 111 | COOCH$_3$ | —(CH$_2$)$_2$— | 1 | H | H | CH$_3$ | |
| 112 | COOCH$_3$ | —(CH$_2$)$_2$— | 1 | H | H | C$_2$H$_5$ | |
| 113 | COOCH$_3$ | —(CH$_2$)$_2$— | 1 | H | H | n-C$_3$H$_7$ | |
| 114 | COOH | —(CH$_2$)$_2$— | 1 | H | H | n-C$_3$H$_7$ | |
| 115 | COOH | —(CH$_2$)$_2$— | 1 | H | H | C$_2$H$_5$ | |
| 116 | COOH | —CH$_2$— | 1 | H | H | C$_2$H$_5$ | NMR see below |
| 117 | COOH | —CH$_2$— | 1 | H | H | n-C$_3$H$_7$ | |
| 118 | COOH | —CH(CH$_3$)CH$_2$— | 1 | H | H | C$_2$H$_5$ | |
| 119 | COOH | —CH(CH$_3$)CH$_2$— | 1 | H | H | n-C$_3$H$_7$ | |
| 120 | COOCH$_3$ | —CH(CH$_3$)CH$_2$— | 1 | H | H | C$_2$H$_5$ | NMR see below |
| 121 | COO—n-C$_3$H$_7$ | —CH(CH$_3$)CH$_2$— | 1 | H | H | C$_2$H$_5$ | |

NMR data

| Compound no. (from Table 1) | $^1$H NMR data (in CDCL$_3$/TMS) [δ] | | |
|---|---|---|---|
| 11 | 0.95 (t) | 1.35 (t) | 3.7 (s) |
| 21 | 0.95 (t) [3 Prot] | 1.35 (t) [3] | 2.95 (t) [2] |
| | 4.15 (g) [2] | | |
| 22 | 0.95 (t) [3] | 2.95 (t) [2] | 4.55 (d) [2] |
| | 5.35 (m) [2] | 6.0 (m) [1] | |
| 29 | 2.95 (t) [3] | 3.65 (t) [3] | 4.10 (g) [2] |
| 30 | 1.2 (m) | 3.70 (s) [3] | 4.55 (d) [2] |
| 31 | 1.30 (t) [3] | 4.11 (g) [2] | |
| 32 | 4.52 (d) [2] | 5.39 (m) [2] | 6.01 (m) [1] |
| 33 | 0.97 (t) [3] | 1.76 (m) [2] | 4.03 (t) [2] |
| 34 | 0.98 (t) [3] | 1.43 (m) [2] | 1.70 (m) [2] |
| | 4.06 (t) [2] | | |
| 35 | 4.54 (d) [2] | 6.12 (m) [1] | 6.37 (d) [1] |
| 37 | 0.9 (t) | 2.3 (t) | 4.1 (q) |
| 49 | 1.4 (s) | 2.4 (t) | 6.1 (m) |

| Compound no. | $^1$H NMR data (in CDCL$_3$/TMS) [δ] | | |
|---|---|---|---|
| 50 | 1.1 (t) | 1.3 (t) | 2.9 (q) |
| 51 | 0.95 (t) | 2.9 (t) | 4.1 (q) |
| 52 | 0.95 (t) | 1.4 (s) | 4.55 (d) |
| 53 | 1.4 (s) | 1.6 (m) | 2.4 (t) |
| 54 | 1.4 (s) | 3.7 (s) | 4.5 (d) |
| 55 | 1.1 (t) | 1.3 (t) | 4.1 (q) |
| 56 | 0.95 (t) | 2.3 (t) | 3.65 (s) |
| 57 | 0.95 (t) | 2.3 (t) | 2.9 (t) |
| 58 | 0.95 (t) | 1.3 (t) | 2.5 (m) |
| 59 | 1.4 (d) | 2.3 (t) | 4.1 (m) |
| 60 | 1.15 (t) | 2.3 (t) | 4.5 (d) |
| 61 | 1.1 (t) | 2.9 (q) | 4.1 (q) |
| 62 | 0.9 (t) | 1.4 (t) | 2.5 (m) |
| 63 | 1.3 (d) | 2.2 (m) | 4.1 (q) |
| 64 | 0.9 (t) | 1.15 (t) | 2.9 (q) |
| (from Table 2) | | | |
| 79 | 0.98 (t) | 3.0 (t) | |
| 80 | 0.92 (t) | 2.95 (t) | 3.65 (s) |

-continued

| Compound no. | ¹H NMR data (in CDCL₃/TMS) [δ] | | |
|---|---|---|---|
| 81 | 1.17 (t) | 2.35 (t) | 3.83 (s) |
| 82 | 1.13 (t) | 3.05 (q) | 3.70 (s) |
| 83 | 0.93 (t) | 3.7 (s) | 3.8 (s) |
| 84 | 0.98 (t) | 1.13 (d) | 2.97 (t) |
| 85 | 1.27 (t) | 1.65 (q) | 3.7 (s) |
| 86 | 1.05 (t) | 1.35 (s) | 3.05 (t) |
| 87 | 1.4 (s) | 1.65 (q) | 3.8 (s) |
| 88 | 1.0 (t) | 3.0 (t) | |
| 89 | 0.9 (t) | 3.6 (s) | 3.7 (s) |
| 90 | 1.0 (t) | 3.1 (t) | 3.7 (s) |
| 91 | 0.95 (t) | 1.4 (s) | 3.0 (t) |
| 106 | 1.3 (m) | 2.5 (m) | 3.1 (q) |
| 108 | 1.0 (t) | 3.0 (q) | |
| 109 | 0.90 (t) | 1.1 (t) | 3.1 (q) |

The cyclohexenone derivatives of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient according to the invention as possible.

For the preparation of solutions, emulsions, pastes and oil dispersions to be sprayed direct, mineral oil fractions of medium to high boiling point, such as kerosene or diesel oil, oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 12 is mixed with 10 parts by weight of N-methyl-alpha-pyrrolidone. A mixture is obtained which is suitable for application in the form of very fine drops.

II. 20 parts by weight of compound no. 1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 2 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 25 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 13 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 17 is intimately mixed with 97 parts by weight of particulate kaolin. A dust is obtained containing 3% by weight of the active ingredient.

VII. 30 parts by weight of compound no. 19 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-form-aldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combatted and their growth stage, and varies from 0.025 to 3 kg/ha, but is preferably from 0.06 to 0.5 kg/ha.

The action of the cyclohexenone derivatives of the formula I on plant growth is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment were 0.06 to 0.5 kg of active ingredient per hectare. No covers were placed on the vessels in this method.

The pots were set up in the greenhouse-species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Alopecurus myosuroides, Avena fatua, Avena sativa, Digitaria sanguinalis, Echinochloa crus-galli, Glycine max., Lolium multiforum, Medicago sativa, Setaria italica, Sinapis alba, Sorghum halepense, Triticum aestivum,* and *Zea mays.*

On preemergence application, compounds nos. 1, 2, 12, 13, 14, 17, 19 and 25 selected by way of example had a herbicidal action on plants from the Gramineae family, whereas *Sinapis alba,* as a dicotyledon representative, remained completely undamaged.

Further, compounds nos. 12 and 14, for example, applied postemergence at a rate of 0.25 kg/ha, had a strong herbicidal action on grasses, whereas soybeans (a dicotyledonous crop) suffered no damage. With 0.5 kg/ha of compounds nos. 1 and 2, volunteer Indian corn and *Setaria italica* as an example of the millet species were selectively combatted in soybeans. In a Gramineae crop such as wheat, the cyclohexenone derivatives of the formula I can be employed as grass herbicides. Compound no. 25 is suitable, at a rate of 0.125 kg/ha, for combatting important grassy weeds.

Compounds nos. 12 and 14, again on postemergence application, had, at low application rates, a strong herbicidal action on common grasses such as *Alopecurus myosuroides* and *Avena fatua.*

Compound no. 32 selected by way of example is suitable for combatting a broad spectrum of grasses in broadleaved crops. The crop plant soybeans, for example, suffered no damage.

In view of the spectrum of weeds which can be combatted, the tolerance of the active ingredients according to the invention by crop plants, the desired influence on the growth of crop plants, and in view of the numerous application methods possible, the cyclohexenone derivatives of the formula I may be used in a large number of crop plants.

The following crops may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | Jerusalem artichoke |

| Botanical name | Common name |
| --- | --- |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the cyclohexenone derivatives of the formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acid derivatives, etc.

It may also be useful to apply the compounds of the formula I, or herbicidal agents containing them, either alone or in combination with other herbicides, in admixture with other crop protection agents, e.g., agents for combatting pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexenone derivative of the formula

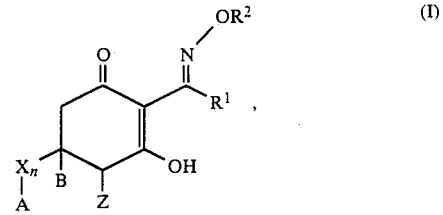

where $R^1$ is methyl, ethyl or n-propyl, $R^2$ is $C_1$-$C_4$-alkyl, unsubstituted or halogen-substituted $C_3$-$C_5$-alkenyl or unsubstituted or halogen-substituted $C_3$-$C_5$-alkynyl, A is trifluoromethyl, B is hydrogen, X is cyclic alkylene of not more than 7 carbon atoms, Z is hydrogen and n is 1, and alkali metal manganese, copper, zinc, iron, calcium, magnesium, barium, ammonium, sulfonium and phosphonium salts thereof.

2. A cyclohexenone derivative of the formula I of claim 1, wherein X is 1,4-cyclohexylene, $R^1$ is n-propyl and $R^2$ is ethyl.

3. The cyclohexenone derivative of the formula I of claim 1, wherein X is 1,2-cyclohexylene, $R^1$ is ethyl and $R^2$ is —$CH_2CH=CH_2$.

4. A cyclohexenone derivative of the formula I as defined in claim 1, wherein the compound is in the form of its sodium or potassium salt.

5. A herbicidal composition containing inert additives and an herbicidal effective amount of cyclohexenone derivative of the formula I as set forth in claim 1.

6. A herbicide as set forth in claim 5, containing from 0.1 to 95 wt% of the cyclohexenone derivative.

7. A herbicide as set forth in claim 6, where the cyclohexenone derivative of the formula I is one in which $R^1$ is $C_2$- or $C_3$-alkyl.

8. A process for combatting unwanted plant growth, wherein the unwanted plants or the area to be kept free from unwanted plant growth are treated with a herbicidally effective amount of a cyclohexenone derivative of the formula I as set forth in claim 1.

9. The process of claim 8, wherein the cyclohexenone derivative is the compound wherein X is 1,4-cyclohexylene, $R^1$ is n-propyl and $R^2$ is ethyl.

10. The process of claim 8, wherein the cyclohexenone derivative is the compound wherein X is 1,2-cyclohexylene, $R^1$ is ethyl and $R^2$ is —$CH_2$—$CH=CH_2$.

11. A carbonyl compound in any one of its tautomeric forms of the formula

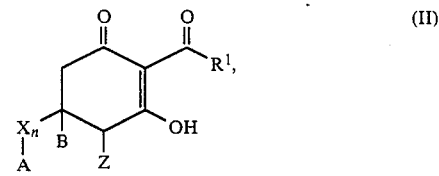

where $R^1$ is methyl, ethyl or n-propyl, A is trifluoromethyl, B is hydrogen, X is cyclic alkylene of not more than 7 carbon atoms, Z is hydrogen, and n is 1.

* * * * *